(12) United States Patent
Malek et al.

(10) Patent No.: US 7,547,805 B2
(45) Date of Patent: Jun. 16, 2009

(54) CATALYTIC PREPARATION OF SEVERELY STERICALLY HINDERED AMINO-ETHER ALCOHOLS USING A METAL LOADED CATALYST

(75) Inventors: Andrzej Malek, Baton Rouge, LA (US); Christine Nicole Elia, Bridgewater, NJ (US); Adeana Richelle Bishop, Baton Rouge, LA (US); Edmund John Mozeleski, Califon, NJ (US); Michael Siskin, Randolph, NJ (US)

(73) Assignee: Exxonmobil Research and Engineering Company, Annandale, NJ (US)

( * ) Notice: Subject to any disclaimer, the term of this patent is extended or adjusted under 35 U.S.C. 154(b) by 231 days.

(21) Appl. No.: 10/587,198

(22) PCT Filed: Feb. 1, 2005

(86) PCT No.: PCT/US2005/003059

§ 371 (c)(1),
(2), (4) Date: Mar. 6, 2007

(87) PCT Pub. No.: WO2005/082834

PCT Pub. Date: Sep. 9, 2005

(65) Prior Publication Data

US 2007/0276162 A1    Nov. 29, 2007

Related U.S. Application Data

(60) Provisional application No. 60/545,197, filed on Feb. 17, 2004.

(51) Int. Cl.
  *C07C 209/16* (2006.01)
  *C07C 209/18* (2006.01)
(52) U.S. Cl. .................. 564/402; 564/403; 564/474; 564/478; 564/479; 564/480
(58) Field of Classification Search .................. None
  See application file for complete search history.

(56) References Cited

U.S. PATENT DOCUMENTS

| | | | |
|---|---|---|---|
| 4,112,051 A | 9/1978 | Sartori et al. |
| 4,112,052 A | 9/1978 | Sartori et al. |
| 4,405,585 A | 9/1983 | Sartori et al. |
| 4,417,075 A | 11/1983 | Stogryn |
| 4,471,138 A | 9/1984 | Stogryn |
| 4,487,967 A | 12/1984 | Stogryn et al. |
| 4,508,692 A | 4/1985 | Savage et al. |
| 4,618,481 A | 10/1986 | Heinzelmann et al. |
| 4,665,195 A | 5/1987 | Stogryn et al. |
| 4,762,934 A | 8/1988 | Stogryn |
| 4,892,674 A | 1/1990 | Ho et al. |
| 4,894,178 A | 1/1990 | Ho et al. |
| 4,961,873 A | 10/1990 | Ho et al. |
| 5,098,604 A | 3/1992 | Brouard et al. |
| 5,098,684 A | 3/1992 | Kresge et al. |
| 5,102,643 A | 4/1992 | Kresge et al. |
| 5,227,353 A | 7/1993 | Apelian et al. |
| 5,250,282 A | 10/1993 | Kresge et al. |
| 5,573,657 A | 11/1996 | Degnan et al. |
| 5,874,623 A | 2/1999 | Adkins et al. |
| 5,936,126 A | 8/1999 | Rühl et al. |
| 5,951,962 A | 9/1999 | Müller et al. |
| 6,238,701 B1 | 5/2001 | Müller et al. |
| 6,248,924 B1 | 6/2001 | Rühl et al. |
| 6,284,917 B1 | 9/2001 | Brunner et al. |

FOREIGN PATENT DOCUMENTS

| | | |
|---|---|---|
| WO | WO 2004/045767 | 6/2004 |
| WO | WO 2004/046076 | 6/2004 |
| WO | WO 2005/081778 | 9/2005 |

OTHER PUBLICATIONS

P. A. Winsor, "Binary and Multicomponent Solutions of Amphiphilic Compounds", Chemical Reviews, Jan. 25, 1968, pp. 1-40, vol. 68, No. 1.

Ulrike Ciesla, Ferdi Schuth, "Ordered mesoporous materials", 1999, pp. 131-149, 27, Elsevier Science B.V., Microporous and Mesoporous Materials.

*Primary Examiner*—Brian J Davis (57) ABSTRACT

The present invention relates to a process for the production of severely sterically hindered amino-ether alcohols using a catalyst based on the combination of one or more catalytically active metals supported in a dispersed form on one or more ordered mesoporous materials as support.

39 Claims, 1 Drawing Sheet

Figure 1

CATALYTIC PREPARATION OF SEVERELY STERICALLY HINDERED AMINO-ETHER ALCOHOLS USING A METAL LOADED CATALYST

This application is the U.S. National Phase filing of PCT Application No. PCT/US2005/003059 filed Feb. 1, 2005, which claims priority to U.S. Provisional Patent Application Ser. No. 60/545,197 filed Feb. 17, 2004.

FIELD OF THE INVENTION

The present invention relates to the production of severely sterically hindered amino-ether alcohols, diaminopolyalkenyl ethers, and mixtures thereof, using a mixture of primary amino and polyalkenyl ether glycol reacted over a catalyst comprising one or more catalytically active metal components deposited on a support, the catalytic process being conducted at elevated temperature and pressure.

DESCRIPTION OF RELATED ART

The catalytic production of severely sterically hindered amino-ether alcohols is already established in the literature. Such severely sterically hindered amino-ether alcohols are made by reacting a primary amino compound, such as tertiary-butyl amine (TBA), with a polyalkenyl ether glycol such as diethylene glycol (DEG) in the presence of a catalytically effective amount of a Group VIII metal containing supported hydrogenation catalyst at elevated temperatures and pressure, such as about 160° C. to about 425° C. and about 50 to about 3,000 psig, as described in U.S. Pat. No. 4,487,967. The reaction of tertiary-butyl amine with diethylene glycol produces ethoxyethanol-tertiary-butyl amine, known as EETB. EETB is useful in gas treating processes for the selective removal of $H_2S$ from gas streams containing mixtures of $H_2S$ and $CO_2$. The use of such severely sterically hindered amino-ether alcohols in such a separation process is described in U.S. Pat. Nos. 4,894,178; 4,405,585; 4,508,692; 4,618,481; 4,112,052; 4,961,873; 4,892,674; 4,417,075.

There is a need, however, for a new process for the production of severely sterically hindered amino-ether alcohols which produce lower level of undesirable by-products and have improved selectively for the desired products. It is an object of the present invention to provide a new catalytic process for the production of severely sterically hindered amino-ether alcohols using a specific class of catalyst which is marked by a high level of conversion of starting materials and selectivity for the desired end product.

SUMMARY OF THE INVENTION

The present invention is directed to a process for the production of severely sterically hindered amino-ether alcohols, diaminopolyalkenyl ethers, and mixtures thereof, preferably predominantly severely sterically hindered amino-ether alcohols by the reaction of a primary amino compound with a polyalkenyl ether glycol over a catalyst comprising one or more catalytically active highly dispersed metals supported on one or more support materials.

The catalyst support material can comprise one or more ordered mesoporous support materials.

The catalytic support material can also comprise one or more ordered mesoporous support materials matrixed or bound with the one or more additional materials selected from the group consisting of conventional amorphous support material, crystalline support material, and mixtures thereof.

The catalyst support material can also comprise one or more ordered mesoporous support materials combined in admixture with the one or more mixed porosity mesoporous support materials.

The catalyst support material can also comprise one or more support materials selected from the group consisting of conventional amorphous support material, crystalline support materials, and mixtures thereof.

The catalytically active metal comprises at least one metal of transition group VIII of the Periodic Table, excluding platinum and palladium (e.g., iron, cobalt, nickel, ruthenium, rhodium, osmium, iridium), either alone or together with at least one additional metal selected from the group consisting of transition group 1B (e.g., copper), group II A (e.g., magnesium), and mixtures thereof, preferably nickel and cobalt, most preferably nickel.

DETAILED DESCRIPTION OF THE INVENTION

In the process of the present invention, a primary amino compound is reacted with a polyalkenyl ether glycol in the presence of a catalyst comprising one or more catalytically active metals dispersed on one or more support materials. The class of support materials identified as ordered mesoporous materials which have a high pore volume, high surface area and controlled pore openings of at least 2 nm are useful for the production of severely sterically hindered amino-ether alcohols. Such mesoporous support materials can be used as such, or combined with additional materials as matrix/binder materials such as macroporous materials, e.g., conventional silica or alumina, or combined with mixed porosity materials as maxtrix/binder materials. Other useful supports for the highly dispersed catalytically active metal are the conventional amorphous and/or crystalline support materials.

The process comprises the batch or continuous production of severely sterically hindered amino ether alcohols by reacting (a) a primary amino compound of the general formula $$R^1\text{---}NH_2$$

wherein $R^1$ is selected from the group consisting of secondary- and tertiary-alkyl radicals having 3 to 8 carbon atoms, cycloalkyl radicals having 3 to 8 carbon atoms, and mixtures thereof, preferably secondary or tertiary alkyl radicals having 4 to 6 carbon atoms, more preferably tertiary alkyl radicals having 4 to 6 carbon atoms, with (b) a polyalkenyl ether glycol of the general formula wherein $R^2$, $R^3$, $R^4$ and $R^5$ are each independently selected from the group consisting of hydrogen, $C_1$-$C_4$ alkyl radicals, and $C_3$-$C_8$ cycloalkyl radicals, with the proviso that if the carbon atom of $R^1$ directly attached to the nitrogen atom is a secondary alkyl radical, at least one of $R^2$ and $R^3$ directly bonded to the carbon which is bonded to the hydroxyl group is an alkyl or cycloalkyl radical, x and y are each positive integers independently ranging from 2 to 4, and Z is from 1 to 10, said process being carried out in the presence of a catalyst comprising one or more catalytically active transition metals of Group VIII of the Periodic Table, excluding platinum and palladium, either alone or together with one or more additional metals selected from the group consisting of either or both main group IIA and transition metal group IB, at elevated temperatures and pressures and wherein the mole ratio of amino compound to polyalkenyl ether glycol is in the range 10:1 to 0.5:1, preferably 5:1 to 1:1, more preferably 3:1 to 1:1, provided that the ratio is less than 2:1 when Z is greater than 1. When Z is 1 the ratio is most preferable between about 3:1 to about 2:1.

Preferably $R^1$ is an alkyl radical having 4 to 6 carbon atoms, $R^2$ and $R^3$ are hydrogen, x and y are 2 and Z is 1. Typical secondary or tertiary alkyl primary amines useful in the present process include isopropyl amine, tertiary-butyl amine, 1-methyl-1-ethyl propyl amine, and tertiary-amyl amine. Most preferably $R^1$ is tertiary-butyl, $R^2$, $R^3$, $R^4$ and $R^5$ are hydrogen, x and y are 2 and Z is 1. When the reactants are so defined the compound produced is predominantly ethoxyethanol tertiary-butyl amine (EETB) with a minor quantity, if any, of co-produced bis(tertiary-butylethoxy)ethane (a diamino polyalkenyl ether).

The reaction of the primary amine compound with the polyalkenyl ether glycol is conducted at a hydrogen pressure charged at room temperature of from about zero to about 300 psig, preferably about 20 to about 200 psig, more preferably about 20 to about 150 psig, at a temperature of about 150 to about 350° C., preferably about 160 to about 300° C., more preferably about 180 to about 225° C., at a total reactor reaction pressure at operating temperature of about 50 to about 1,500 psig, preferably about 50 to about 1000 psig, more preferably about 50 to about 500 psig. The time the reaction is run is important in terms of by-product formation. The actual time required in a particular reaction will vary and is dependent upon the specific reactants, temperature and pressure used, as well as the size of the batch being processed. Long reaction times generally favor by-product formation, as do higher reaction temperatures. In general, the reaction is run for a time ranging from about 0.5 to about 24 hours, preferably about 1 to about 12 hours, more preferably about 2 to about 8 hours.

In the present process the concentration of the catalyst comprising one or more catalytically active highly dispersed metals supported on one or more support materials is that which is sufficient to promote the catalytic conversion of the primary amine and the polyalkenyl ether glycol into the severely sterically hindered amino-ether alcohol, diaminopolyalkenyl ether, and/or mixtures thereof. Thus, the amount of catalyst present with respect to the total amount of reactant will generally range from about 0.001 to about 10 wt %, preferably about 0.01 to about 8 wt %, more preferably about 0.01 to about 5 wt % catalyst based on the weight of the total reactant charge.

The reaction may be conducted in any reactor vessel capable of withstanding the pressures and temperatures necessary to carry out the process. The reactants can be mixed with the catalyst and reacted in a batch process. The catalyst in the reactor can be slurried in the reaction mixture or encased in a basket. Alternatively, the reactants can be passed over a fixed bed of the catalyst, either co-currently or countercurrently. Other reactors suitable for use include moving bed reactors and continuously stirred reactors. For example, in a continuous stirred reactor the catalyst is circulated and the reactants and reaction products are passed through the reaction vessel at a controlled rate.

The reaction can be carried out in the absence of any added solvent, the liquid reactants functioning as the liquid reaction medium to facilitate reaction. However, an inert solvent can be included in the reaction medium.

Typical solvents include linear or cyclic ethers or hydrocarbon-containing compound in which the reactants will dissolve, in an excess secondary- or tertiary-alkyl amine reagent. The solvent should be relatively low molecular weight to facilitate removal from the product of the reaction. The amount of the solvent may vary, but will generally range from about 10 to 50 wt %, preferably from about 15 to 30 wt % based on the weight of the reactants used. Examples of typical solvents include dimethylether, ethylene glycol dimethyl ether, toluene, tetrahydrofuran. Because excess amine reagent can function as solvent, excess isopropyl amine, tertiary-butyl amine, tertiary-amyl amine and the like can be present in the reactor functioning as solvent. The preferred solvents include tetrahydrofuran, dimethylether, ethylene glycol dimethylether and toluene.

The catalyst employed is one or more dispersed reduced metals on one or more support materials, one or more dispersed reduced metals on one or more mesoporous support materials, one or more dispersed reduced metals on one or more mesoporous support materials, combined in admixture with one or more macroporous support materials, the one or more macroporous support materials being a matrix or binder, or one or more dispersed reduced metals on one or more mesoporous support materials combined in admixture with one or more mixed porosity materials, or one or more dispersed reduced metals on one or more conventional amorphous support materials and/or crystalline support materials.

For the purposes of the present invention, the terms "macropores" and "mesopores" are used as they are defined in Pure Appl. Chem., 45 (1976), 79, namely as pores whose diameter is above 50 nm (macropores) or whose diameter is from 2 nm and 50 nm (mesopores). In the process of the present invention the one or more catalytically active metals are deposited on a specific catalyst support.

The support may comprise one or more ordered mesoporous materials with a unique structure and pore geometry as described below. Preferred ordered mesoporous materials are inorganic, porous, non-layered materials which, in their calcined forms exhibit an X-ray diffraction pattern with at least one peak at a d-spacing greater than about 18 Angstrom Units (Å). They also have a benzene adsorption capacity of greater than 15 grams of benzene per 100 grams of the material at 50 torr and 25° C. Preferred ordered mesoporous materials that may be used in the present invention, are those ordered mesoporous materials that may be synthesized using amphiphilic compounds as directing agents. Examples of such materials are described in U.S. Pat. No. 5,250,282, the whole contents of which are hereby incorporated by reference. Examples of amphiphilic compounds are also provided in Winsor, Chemical Reviews, 68(1), 1968. Other suitable ordered mesoporous materials of this type are also described in "Review of Ordered Mesoporous Materials", U. Ciesla and F. Schuth, Microporous and Mesoporous Materials, 27, (1999), 131-49. Such materials include but are not limited to materials designated as SBA (Santa Barbara) such as SBA-2, SBA-15 and SBA-16, materials designated as FSM (Folding Sheet Mechanism) such as FSM-16 and KSW-2, materials designated as MSU (Michigan State) such as MSU-S and MSU-X, materials designated as TMS or Transition Metal Sieves, materials designated as FMMS or functionalized monolayers on mesoporous supports and materials designated as APM or Acid Prepared Mesostructure. In a preferred form, the support material is characterized by a substantially uniform hexagonal honeycomb microstructure with uniform pores having a cell diameter greater than 2 nm and typically in the range of 2 to 50 nm, preferably 3 to 30 nm and most preferably from 3 to 20 nm. Particularly preferred ordered mesoporous materials are the silicate or alumino-silicate ordered mesoporous materials designated as M41S such as MCM-41, MCM-48 and MCM-50. Mixtures of these materials can be used. These ordered mesoporous materials are described in detail in U.S. Pat. No. 5,102,643, the whole contents of which are hereby incorporated by reference. A particularly suitable sub-class of this family of materials for use in the present invention are the mesoporous silicas designated as MCM-41 and MCM-48. Most prominent among these materials is an ordered mesoporous material identified as MCM-41, which is usually synthesized as a metallosilicate with Broensted acid sites by incorporating a tetrahedrally coordinated trivalent element such as Al, Ga, B, or Fe within the silicate framework. The preferred forms of these materials are the aluminosilicates although other metallosilicates may also be utilized. MCM-41 is characterized by a microstructure with a uniform, hexagonal arrangement of pores with diameters of at least about 2 nm: after calcination it exhibits an X-ray diffraction pattern with at least one d-spacing greater than about 18 Å and a hexagonal electron diffraction pattern that can be indexed with a $d_{100}$ value of greater than about 18 Å, which corresponds to the d-spacing of the peak in the X-ray diffraction pattern. The MCM-41 molecular sieves generally have a $SiO_2/Al_2O_3$ molar ratio when alumina is present that is greater than 100, preferably greater than 200, and most preferably greater than 300. This material is described below and in detail in Ser. No. 07/625,245, now U.S. Pat. No. 5,098,684 (Kresge et al) and U.S. Pat. No. 5,102,643 to Kresge et al, both of which are incorporated by reference herein in their entirety.

The ordered mesoporous materials may be crystalline, that is having sufficient order to provide a diffraction pattern such as, for example, by X-ray, electron or neutron diffraction, following calcination, with at least one peak. These mesoporous materials may be characterized by their structure, which includes large pore windows as well as high sorption capacities.

Ordered mesoporous materials as used herein can be distinguished from other porous inorganic solids by the regularity of their large open pores, whose pore size more nearly resembles that of amorphous or paracrystalline materials, but whose regular arrangement and uniformity of size (pore size distribution within a single phase of, for example, +/−25%, usually +/−15% or less of the average pore size of that phase) resemble more those of crystalline framework materials such as zeolites. The term "hexagonal" is intended to encompass not only materials that exhibit mathematically perfect hexagonal symmetry within the limits of experimental measurement, but also those with significant observable deviations from that ideal state. A working definition as applied to the microstructure of the ordered mesoporous support material would be that most channels in the material would be surrounded by six nearest neighbor channels at roughly the same distance. Defects and imperfections will cause significant numbers of channels to violate this criterion to varying degrees, depending on the quality of the material's preparation. Samples which exhibit as much as +/−25% random deviation from the average repeat distance between adjacent channels still clearly give recognizable images of the present ordered mesoporous materials.

The ordered mesoporous materials as used for preparation of the catalyst support preferably have the following composition:

wherein W is a divalent element, such as a divalent first row transition metal, e.g., manganese, cobalt and iron, and/or magnesium, preferably cobalt; X is a trivalent element, such as aluminium, boron, iron and/or gallium, preferably aluminium; Y is a tetravalent element such as silicon and/or germanium, preferably silicon; Z is a pentavalent element, such as phosphorus; M is one or more ions, such as, for example, ammonium, Group IA, IIA and VIIB ions, usually hydrogen, sodium and/or fluoride ions; n is the charge of the composition excluding M expressed as oxides; q is the weighted molar 1 average valence of M; n/q is the number of moles or mole fraction of M; a, b, c, and d are mole fractions of W, X, Y and Z, respectively; h is a number of from 1 to 2.5; and (a+b+c+d)=1. A preferred embodiment of the above crystalline material is when (a+b+c) is greater than d, and h=2. A further embodiment is when a and d=0, and h=2. In the as-synthesized form, the mesoporous material has a composition, on an anhydrous basis, expressed empirically as follows:

wherein R is the total organic material not included in M as an ion, and r is the coefficient for R, i.e. the number of moles or mole fraction of R. The M and R components are associated with the material as a result of their presence during synthesis of the material and are easily removed or, in the case of M, replaced by post-synthesis methods hereinafter more particularly described.

To the extent desired, the original M, e.g., ammonium, sodium or chloride, ions of the as-synthesized material can be replaced in accordance with techniques well known in the art, at least in part, by ion exchange with other ions. Preferred replacing ions include metal ions, hydrogen ions, hydrogen precursor, e.g., ammonium, ions and mixtures thereof. Other ions include rare earth metals and metals of Groups IA (e.g., K), IIA (e.g., Ca), VIIA (e.g., Mn), VIIIA (e.g., Ni), IB (e.g., Cu), IIB (e.g., Zn), IIIB (e.g., In), IVB (e.g., Sn), and VIIB (e.g., F) of the Periodic Table of the Elements (Sargent-Welch Co. Cat. No. S-18806, 1979) and mixtures thereof.

The preferred ordered mesoporous materials for use in the process of the present invention are ordered mesoporous silicas. The most preferred ordered mesoporous silicas are those designated as M41S, with the most preferred being MCM-41.

Examples of mesoporous materials that may be used in the process of the present invention are the mesoporous silicas as described in and prepared according to U.S. Pat. No. 5,951,962, the disclosure of which is incorporated herein in its entirety. In that embodiment, mesoporous silica is prepared by converting a silica precursor in a water and polymer dispersion containing reaction medium. The preferred polymer dispersion is a cationic polymer.

High surface area mesoporous alumina solids may also be used in preparing the catalyst supports for use in the processes of the present invention; such high surface area mesoporous alumina solids may be prepared according to the methods described in U.S. Pat. No. 6,238,701, the disclosure of which is incorporated herein in its entirety.

The support may also consist of conventional amorphous and/or cyrstaline macroporous materials. Materials that are both macroporous and mesoporous, such as those described in U.S. Pat. Nos. 5,936,126, 6,248,924 and 6,284,917 the disclosures of which are incorporated herein by reference in their entirety may also be employed as suitable catalyst support. These materials can be used as supports by themselves or in combination with each other or with the mesoporous and/or ordered mesoporous materials previously described in preparing catalysts useful in the present process.

Conventional amorphous and/or crystalline macroporous materials suitable for use as supports themselves or as matrix or binder materials have a mean pore diameter of at least about 50 nm, preferably at least about 100 nm, in particular at least about 500 nm. Preferably these macroporous materials have a BET surface area that is at most about 30 $m^2/g$, preferably at most about 15 $m^2/g$, more preferably at most about 10 $m^2/g$ in particular at most about 5 $m^2/g$ and more preferably at most about 3 $m^2/g$. The mean pore diameter of theses macroporous materials is preferably from about 100 nm to about 20000 nm, and more preferably from about 500 nm to about 5000 nm, and most preferably 500 nm to 1000 nm. The surface area of these macroporous materials is preferably from about 0.2 to about 15 $m^2/g$, more preferably from about 0.5 to about 10 $m^2/g$, in particular from about 0.5 to about 5 $m^2/g$ and more preferably from about 0.5 to about 3 $m^2/g$. Such macroporous material can be used in admixture with the mesoporous support material.

The surface area of the conventional amorphous and/or crystalline macroporous materials and mixed porosity materials may be determined by the BET method using $N_2$ adsorption, in particular in accordance with DIN 66131. The mean pore diameter and the size distribution may be determined by $N_2$ porosimetry. The BJH adsorption isotherms are measured using ASTM method D-4222, "Standard test method for determination of nitrogen adsorption and desorption isotherms of catalysts by static volumetric measurements".

The conventional amorphous and/or crystalline macroporous materials and mixed porosity materials that may be used as such as supports are, for example, macropore containing activated carbon, silicon carbide, aluminum oxide, silicon dioxide, titanium dioxide, zirconium dioxide, magnesium oxide, zinc oxide or mixtures of two or more thereof, with preference being given to using macropore containing aluminum oxide (alumina), silicon dioxide (silica), and mixtures thereof, preferably silica.

When a mesoporous and/or ordered mesoporous material is used in combination with macroporous material and/or mixed porosity matrix material, the finished catalyst may be a composition comprising a support matrix of from 90 to 10% by weight mesoporous material and 10 to 90% by weight macroporous material, preferably 80 to 20% by weight mesoporous material and 20 to 80% by weight macroporous material, more preferably 80 to 40% by weight mesoporous and 20 to 60% by weight of macroporous material. A particularly preferred composition comprises a support matrix of 70 to 60%, ideally 65% by weight mesoporous material and 30 to 40%, ideally 35% by weight macroporous material.

In the present process the final catalyst may consist solely of one or more reduced metals deposited on the surfaces of one or more of the previously described support materials. It is preferred that the catalyst used in the present process comprises one or more reduced metals deposited on one or more mesoporous and/or ordered mesoporous support materials. The catalyst can be free of added inorganic binder but the use of the catalyst in the bound form is also encompassed. The supports with or without reduced metal deposited thereon may be shaped into a wide variety of particle sizes. Generally, the particles can be in the form of a powder, a granule, or a molded product, such as an extrudate having particle size sufficient to pass through a 2 mesh (Tyler) screen and be retained on a 400 mesh (Tyler) screen. In cases where the catalyst is molded, such as by extrusion, they can be extruded before drying or partially dried and then extruded. In these embodiments various extrusion or forming aids may be used in the extrusion or forming process along with one or more solvents, all techniques which are well known in the art.

The support material with or without one or more catalytic metals deposited thereon may be formed into composites with inorganic binder or matrix materials that are resistant to the temperatures and other conditions employed in the present processes. Such binder or matrix materials may also aid in the formation and manufacture of the final catalyst. Such binder or matrix materials include active and inactive materials and synthetic or naturally occurring zeolites as well as inorganic materials such as clays and/or oxides such as alumina, silica or silica-alumina. The latter may be either naturally occurring or in the form of gelatinous precipitates or gels including mixtures of silica and metal oxides. Use of a material in conjunction with the zeolite, i.e., combined therewith or present during its synthesis, which itself is catalytically active may change the conversion and/or selectivity of the catalyst. These materials may be incorporated into naturally occurring clays, e.g., bentonite and kaolin, to improve the crush strength of the catalyst under commercial operating conditions and function as binders or matrices for the catalyst. The support containing one or more catalytic metals may be formed into a composition comprising the macroporous matrix material in amounts from 99:01 to 05:95 by weight, preferably from 99:01 to 10:90, more preferably from 99:01 to 20:80, and most preferably from 99:01 to 50:50, catalyst support to matrix material. Preferably, if used, the additional matrix material is kept to a minimum typically less than 50 wt % of the combined weight of catalyst support and matrix material, ideally less than 40 wt %, preferably less than 30 wt %, more preferably less than 20 wt %, more preferably less than 15 wt %, most preferably less than 10 wt % and in a most preferred embodiment less than 5 wt %. Formation of the composition may be achieved by conventional means including mulling the materials together followed by extrusion of pelletizing into the desired finished catalyst particles. Ideally the additional binder matrix material is selected from the previously described conventional amorphous and/or crystalline macroporous material or is a material of mixed porosity, i.e., both macroporous and mesoporous.

The catalyst includes a reduced metal as the catalytic component. The catalytic component is provided by a metal or combination of metals. Catalytic metals that may be used are preferably one or more metals of transition group VIII of the Periodic Table, excluding platinum and palladium, alone or in combination with one or more metals of Group IB and may also be combined with one or more metals from main group IIA. Preferably, the catalytic metal is selected from the group consisting of nickel, iron, cobalt, osmium, iridium, ruthenium, rhodium, and mixtures thereof, preferably nickel, iron, cobalt and mixtures thereof, more preferably nickel and cobalt, most preferably nickel, which can be in combination with an additional catalytic component selected from the group consisting of copper, silver, gold and mixtures thereof, preferably copper, and may further contain an additional metal selected from the group consisting of beryllium, magnesium, calcium, strontium, barium, and mixtures thereof, preferably magnesium, calcium and mixtures thereof, more preferably magnesium. Preferred the catalytic metals include, nickel; nickel and cobalt; nickel and copper; nickel, copper and magnesium; nickel, cobalt and magnesium; more preferably nickel.

The catalyst generally comprises from about 2.5 to 80 wt %, preferably about 10 to 65 wt % reduced metal on the support material based on the total weight of the reduced catalyst. In the case of nickel, it is preferred that the amount of reduced metal be at least 10%, preferably at least about 12%, more preferably at least about 14% based on the total weight of the reduced catalyst.

The mesoporous support materials and especially MCM-41 are preferred notably because of their very high surface areas allowing for relatively higher metal loading while maintaining high metal dispersions. The catalytic metal component can be exchanged onto the support material, impregnated into it or physically admixed with it but exchange or impregnation are preferred.

In the case of catalysts which have a plurality of active metals applied to the support, the metal salts or metal salt solutions can be applied simultaneously or in succession.

When the ordered mesoporous material is used in combination with a macroporous and/or mixed porosity matrix material it is preferred that the metal component is applied to the ordered mesoporous material after it is combined with the matrix material.

The catalyst is manufactured using a process in which a support is provided with one or more catalytically active metal sites through the use of a specific sequence of process steps. In the first step the support is provided with one or more organic complexes of one or more metals and in a second step the organic complex is either fully or partially decomposed.

In one embodiment a compound, or salt, of one or more catalytic metals is combined with one or more organic compounds to form a mixture which is then contacted with a support to deposit the organic complex. In this embodiment the complex may be formed on formation of the mixture or may be formed after contact with the support and after removal of any solvent or solvents used during formation of the mixture. In another embodiment the support is first contacted with a compound, or salt, of one or more catalytic metals followed by treatment with one or more organic compounds to form the organic complex on the support. In an alternative embodiment the support is first contacted with one or more organic compounds followed by treatment with one or more compounds, salt, or mixtures thereof, of one or more catalytic metals to form the complex on the support. In a further embodiment one or more organic compounds and one or more compounds, and/or salts, of one or more catalytic metals are contacted simultaneously with the support to form the organic complex. In yet a further embodiment a suitable organic complex of the desired metal may be synthesized and applied to the support via solution of the complex in a suitable solvent for the complex. In all instances, however, the support is contacted with an organic complex of one or more catalytic metals, regardless of the sequence used to bring the organic compound and the catalytic metal salt into contact with each other and the resulting complex into contact with the support.

Suitable catalytic metal salts for preparing the metal salt solutions are for example nitrates, nitrosyl nitrates, halides, carbonates, carboxylates, acetylacetonates, chloro complexes, nitrito complexes or amine complexes of the corresponding metals, with preference being given to the nitrates and nitrosyl nitrates and most preferably the nitrates.

Any organic compounds that are capable of forming organic complexes with the one or more salts or compound of the metals may be used. Typically these will be organic compounds that are capable of forming complexes that are stable under the conditions that are normally used for depositing catalytic metals. Ideally, the organic compounds are selected to provide metal organic complexes that are stable under the conditions normally used for drying catalyst supports after impregnation with one or more of the catalytic metals. Suitable organic compounds are well known in the art of transition metal chemistry and include such organic compounds as organic chelating agents, organic monodentate, bidentate and polydentate ligands commonly used in the preparation of transition metal coordination complexes. In a number of such complexes one or more ligands being covalently bonded molecules and/or ions may be present in the complex. The organic compound may also be one or more of the organic compounds used in the manufacture of the support or present during its synthesis. The catalytic metal salt, the organic compound, the organic complex of organic compound and catalytic metal salt, in any sequence or simultaneously in the case of the separate organic compound and catalytic metal salt can be exchanged onto the support by impregnation or physical admixture. This can be achieved by steeping the support in the appropriate solution or by dipping, spraying or any other suitably technique.

Particularly suitable organic compounds are compounds that contain one or more amino groups such as amines or amino acids and most preferably organic compounds containing both amino and alcohol groups.

The compounds containing one or more amino groups may be aliphatic amines, cycloaliphatic amines, aralkyl amines and alkylaryl amines. These may be primary, secondary and tertiary amines. They may also be quaternary ammonium salts with a counter ion. It is preferred that the nitrogen-containing compound is one or more primary, secondary or tertiary amines, preferably one or more aliphatic amines and most preferably one or more amines having one or more hydroxyl groups such as for example hydroxyalkylamines. At least one of the amines used in an aliphatic amine and it is preferred that that aliphatic amine contain one or more hydroxyl groups.

The nitrogen-containing compound used according to the present invention has the following general formula:

$$NR^1R^2R^3 \qquad (I)$$

wherein $R^1$, $R^2$ and $R^3$ independently are one or more of the following groups: $C_1$-$C_{50}$-alkyl, $C_3$-$C_{50}$-cycloalkyl, aromatic, alkyl substituted aromatic, such as $C_1$-$C_{50}$-alkyl substituted aromatic, aromatic substituted aliphatic moieties such as $C_1$-$C_{50}$-alkylene moieties substituted with one or more aromatic groups, $C_1$-$C_{50}$-hydroxyalkyl, amino- and/or hydroxyl-substituted $C_1$-$C_{50}$-alkyl, alkoxyalkyl such as $C_2$-$C_{50}$-alkoxyalkyl, dialkylaminoalkyl such as $C_3$-$C_{50}$-dialkylaminoalkyl, alkylaminoalkyl such as $C_2$-$C_{50}$-alkylaminoalkyl, heterocyclic, aromatic heterocyclic, alkyl substituted heterocyclic and alkyl substituted aromatic heterocyclic, such as $C_1$-$C_{50}$-alkyl substituted heterocyclic and aromatic heterocyclic compounds, and heterocyclic substituted aliphatic moieties such as $C_1$-$C_{50}$-alkylene moieties substituted with one or more aromatic groups. In addition, $R^1$ and $R^2$ may independently be hydrogen. In another embodiment, $R^1$ and $R^2$ may form, with the nitrogen atom, a nitrogen-containing heterocycle, aromatic heterocycle, alkyl substituted heterocycle or alkyl substituted aromatic heterocycle.

Examples of alkyl groups include; methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, n-heptyl, isoheptyl, n-octyl, isooctyl, 2-ethylhexyl, n-decyl, 2-n-propyl-n-heptyl, n-tridecyl, 2-n-butyl-n-nonyl and 3-n-butyl-n-nonyl, particularly preferably ethyl, isopropyl, 2-ethylhexyl, n-decyl, 2-n-propyl-n-heptyl, n-tridecyl, 2-n-butyl-n-nonyl and 3-n-butyl-n-nonyl, and $C_{40}$-$C_{200}$-alkyl such as polybutyl, polyisobutyl, polypropyl, polyisopropyl and polyethyl. The most preferred aliphatic amines are aliphatic amines having one or more alkyl groups having 1 to 20 carbon atoms and more preferably 2 to 14 carbon atoms.

Examples of cycloalkyl groups include $C_3$-$C_{12}$-cycloalkyl, preferably $C_3$-$C_8$-cycloalkyl such as cyclopropyl, cyclobutyl, cyclopentyl, cyclohexyl, cycloheptyl and cyclooctyl.

Examples of aromatic groups include; phenyl, 1-naphthyl, 2-naphthyl, 1-anthryl, 2-anthryl and 9-anthryl, 1-phenanthryl, 2-phenanthryl, 3-phenanthryl, 4-phenanthryl and 9-phenanthryl.

Examples of alkyl substituted aromatic groups include $C_7$-$C_{50}$ alkyl aromatic groups, preferably $C_7$-$C_{40}$-alkylphenyl such as 2-nonylphenyl, 3-nonlyphenyl, 4-nonylphenyl, 2-decylphenyl, 3-decylphenyl, 4-decylphenyl, 2,3-dinonylphenyl, 2,4-dinonylphenyl, 2,5-dinonylphenyl, 3,4-dinonylphenyl, 3,5-dinonylphenyl, 2,3-didecylphenyl, 2,4-didecylphenyL, 2,5-didecylphenyl, 3,4-didecylphenyl and 3,5-didecylphenyl, more preferably $C_7$-$C_{12}$ alkylphenyl such as 2-methylphenyl, 3-methylphenyl, 4-methylphenyl, 2,4-dimethylphenyl, 2,5-dimethylphenyl, 2,6-dimethylphenyl, 3,4-dimethylphenyl, 3,5-dimethylphenyl, 2,3,4-trimethylphenyl, 2,3,5-trimethylphenyl, 2,3,6-trimethylphenyl, 2,4,6-trimethylphenyl, 2-ethylphenyl, 3-ethylphenyl, 4-ethylphenyl, 2-n-propylphenyl, 3-n-propylphenyl and 4-n-propylphenyl.

Examples of aromatic substituted aliphatic moieties include $C_7$-$C_{50}$ alkylene moieties substituted with one or more aromatic substituents, preferably $C_7$-$C_{12}$-phenylalkyl such as benzyl, 1-phenethyl, 2-phenethyl, 1-phenylpropyl, 2-phenylpropyl, 3-phenylpropyl, 1-phenylbutyl, 2-phenylbutyl, 3-phenylbutyl and 4-phenylbutyl, particularly preferably benzyl, 1-phenethyl and 2-phenethyl.

Examples of hydroxyalkyl groups include $C_1$-$C_{50}$-hydroxyalkyl, preferably $C_1$-$C_8$-hydroxyalkyl, particularly preferably $C_1$-$C_4$-hydroxyalkyl such as hydroxymethyl, 1-hydroxyethyl, 2-hydroxyethyl, 1-hydroxy-n-propyl, 2-hydroxy-n-propyl, 3-hydroxy-n-propyl and 1-hydroxy-methylethyl. Particularly preferred hydoxyalkyl group containing nitrogen compounds include the mono-, di-, and tri-, substituted aliphatic hydroxyalkylamines such as methanolamine, di-methanolamine, tri-methanolamine, ethanolamine, di-ethanolamine, tri-ethanolamine, butanolamine, di-butanolamine, tri-butanolamnine, propanolamine, di-propanolamine, and tri-propanolamine.

Examples of amino- and hydroxyalkyl groups include $C_1$-$C_{50}$-alkyl, preferably amino- and/or hydroxyl-substituted $C_1$-$C_8$-alkyl, particularly preferably amino and/or hydroxyl-substituted $C_1$-$C_4$-alkyl such as N-(hydroxyethyl)aminoethyl and N-(aminoethyl)aminoethyl.

Examples of alkoxyalkyl groups include $C_2$-$C_{50}$-alkoxyalkyl, preferably $C_2$-$C_{20}$-alkoxyalkyl, particularly preferably $C_2$-$C_8$-alkoxyalkyl such as methoxymethyl, ethoxymethyl, n-propoxymethyl, isopropoxymethyl, n-butoxymethyl, isobutoxymethyl, sec-butoxymethyl, tert-butoxymethyl, 1-methoxyethyl and 2-methoxyethyl, particularly preferably $C_2$-$C_4$-alkoxyalkyl such as methoxymethyl, ethoxymethyl, n-propoxymethyl, isopropoxymethyl, n-butoxymethyl, isobutoxymethyl, sec-butoxymethyl, tert-butoxymethyl, 1-methoxyethyl and 2-methoxyethyl.

Examples of dialkylamino groups include $C_3$-$C_{50}$-dialkylaminoalkyl, preferably $C_3$-$_{20}$-dialkylaminoalkyl, particularly preferably $C_3$-$C_{10}$-dialkylaminoalkyl such as dimethylaminomethyl, dimethylaminoethyl, diethylaminoethyl, di-n-propylaminoethyl and diisopropylaminoethyl.

Examples of alkylaminoalkyl groups include $C_2$-$C_{50}$-alkylaminoalkyl, preferably $C_2$-$C_{20}$-alkylaminoalkyl, particularly preferably $C_2$-$C_8$-alkylaminoalkyl such as methylaminomethyl, methylaminoethyl, ethylaminomethyl, ethylaminoethyl and iso-propylaminoethyl.

Examples of aromatic heterocycles include 2-pyridinyl, 3-pyridinyl, 4-pyridinyl, pyrazinyl, 3-pyrrolyl, 2-imidazolyl, 2-furanyl and 3-furanyl. Examples of alkyl substituted aromatic heterocycles include $C_4$-$C_{50}$-mono-hetarylalkyl, such as 2-pyridylmethyl, 2-furanyl-methyl, 3-pyrrolylmethyl and 2-inidazolylmethyl, and $C_4$-$C_{50}$-alkylhetaryl such as 2-methyl-3-pyridinyl, 4,5-dimethyl-2-imidazolyl, 3-methyl-2-furanyl and 5-methyl-2-pyrazinyl.

Examples of dialkylaminoalkyl groups include $C_3$-$C_{50}$-dialkylaminoalkyl, preferably $C_3$-$C_{16}$-dialkylaminoalkyl such as dimethylaminomethyl, dimethylaminoethyl, diethylaminoethyl, di-n-propylaminoethyl and diisopropylaminoethyl.

Examples of heterocyclic compounds, include pyridine, pyrrole, imidazole, oxazole, thiazole, pyrazole, 3-pyrroline, pyrrolidine, pyrimidine, and substituted examples of these heterocyclic compounds. Examples of organonitrile compounds include acrylonitrile, alkyl nitrites such as for example methyl nitrile, and ethyl nitrile.

Suitable amino acids include natural and synthetic amino acids. The natural amino acids include all isomers of the following: alanine, arginine, asparagines, aspartic acid, cysteine, cystine, 3, 5-dibromotyrosine, 3,5,diiodotyrosine, glutamic acid, glutamine, glycine, histidine, hydroxylysine, hydroxyproline, isoleucine, leucine, lysine, methionine, phenylalanine, proline, serine, threonine, thyroxine, tryptophane, tyrosine and valine, a particularly preferred amino acid is L-arginine.

The preferred organic compounds for forming the organic complex are organic nitrogen containing compounds, more preferably amines, and more preferably amines containing one or more alcohol groups.

The organic compound may be introduced into the manufacture or synthesis of the support. The organic compound may be an organic template as used in the synthesis of the support when the support is a molecular sieve. Such organic templates are well known in the art and are preferably nitrogen containing organic templates, especially nitrogen containing organic templates, which further comprise hydroxyl functionality. The organic compound may be introduced in addition to any organic template during the manufacture or synthesis of the support. In all aspects when either or all components for the preparation of the organic complex are incorporated into or within the support or the organic complex itself is incorporated into or within the support, the support may be used in the green state.

The organic compound may be used at any suitable level in relation to the amount of salt or compound of the catalytic metal. The organic compound may be present in excess of that required to form the organic complex. Ideally the compounds are used at an appropriate mole ratio to convert all of the salt or compound of the catalytic metal to one or more organic complexes. This may be a molar ratio of 1:1 or higher depending on the capacity of the metal to complex with the organic compound, the capacity of the organic compound to complex with the metal and the presence of other complexing ligands such as monodentate ligands. However it is possible to use levels of organic compound which are insufficient to complex with all of the catalytic metal; in these circumstances not all of the metal is converted to organic complex and the resulting catalyst may contain catalytic metal sites that have been derived from complexed and non-complexed metal intermediates. Ideally, the mole ratio of organic compound to catalytic metal is within the molar ratio range of 0.1:1 to 40:1, preferably, 0.1:1 to 30:1, more preferably 0.2:1 to 25:1, even more preferably 0.5:1 to 10:1, most preferably 0.5:1 to 5:1. Excess organic compound may be present when the organic compound is incorporated into or within the support during manufacture or synthesis of the support.

When the complex is formed in a mixture before contact with the support the mixture is usually and preferably formed in combination with a solvent, which may be water or an organic solvent or a mixture of water and solvent. The amount of solvent used may vary within wide ranges but is typically sufficient to ensure that the mixture may be effectively contacted with the support so as to wet the support and when the support is porous to allow penetration of the mixture into the porous support. Typically the salt or compound of one or more of the catalytic metals and the organic compound(s) are used in amounts which depending on their form allow the required mole ratios indicated above to be achieved in the mixture. The remainder of the mixture comprises one or more solvents which may be present in an amount from 1 to 99 wt % of the weight of the total mixture, preferably 5 to 90 wt % of the weight of the total mixture, more preferably 5 to 80 wt % of the weight of the total mixture, even more preferably 10 to 70 wt % of the weight of the total mixture and most preferably 10 to 65 wt % of the weight of the total mixture. Additional solvents may also be used in order to facilitate application of one or more of the components required to manufacture the catalyst.

After formation of the organic complex on the support the support may and preferably is dried to remove most of the solvent and/or water present during formation of the complex. Drying may be achieved under ambient conditions such as room temperature or this may be achieved at elevated temperatures, preferably drying is at a temperature from 100 to 150° C. Preferably, little or no decomposition of the organic complex occurs during the drying phase and drying merely results in the removal of non-complexed volatile materials. If desired, the metal loaded supports can be calcined at from 200 to 600° C., preferably from 350 to 450° C.

Once the support containing one or more organic complexes has been prepared the support is treated so as to fully or partially decompose the organic complex on the support. Although not wishing to be bound by any theory it is believed that this full or partial decomposition results in the formation in-situ of one or more precursors to the catalytically active metal sites. It is believed that it is, in part, the formation of these precursors and their subsequent conversion that ensures that in these aspects the final catalyst exhibits a high degree of catalytic activity and has high levels of metal dispersion within the catalyst. An important parameter in the activity of catalytic metals is the form of the metal on the support and the level of dispersion of the metal on the support. The process of the present invention produces catalysts that comprise catalytically active metal sites that are relatively small and highly dispersed. In addition the level of dispersion is relatively stable.

"Partial decompositions" means that the chemical composition of the organic complex is varied; this may be due to a change in the structure of the organic complex or may be due to the chemical destruction of part of or a component of the complex. When the destruction is partial the method of destruction is selected to ensure that the removal of non-metal chemical species associated with the complex is incomplete. When the destruction is complete the only significant element of the complex remaining would be the one or more catalytic metals as oxides when destruction is carried out under oxidizing conditions or the reduced metal when the destruction is carried out in the presence of hydrogen. There may also be residues such as carbon residues formed from decomposition of the organic complex. The partial decomposition is due to variations in structure and/or composition that do not normally occur under the drying conditions typically used in catalyst preparation methods. The changes of structure and/or composition under the conditions of the second stage may be detected and monitored using various analytical techniques that are well known in the art such as infra-red spectroscopy, mass spectroscopy, thermogravimetric analysis, gas or liquid chromatography and spectroscopy.

A variety of methods may be used to induce partial or full destruction of the organic complex. These include chemical methods such as chemically induced hydrolysis or decomposition such as by the treatment with acid or base or ozone or similar chemical active materials. Other methods for inducing full or partial decomposition include thermal methods such as pyrolysis and/or calcination, both of which are the preferred methods with particular preference being given to calcination. A further method is treatment with steam. In one embodiment the pyrolysis may be carried out in the presence of hydrogen; in that instance any subsequent treatment with hydrogen may be omitted.

When calcination or pyrolysis is used as the method for full or partial decomposition of the organic complex the exact conditions used will depend on the nature of the complex and especially its thermal stability and decomposition profile under elevated temperature. By using thermogravimetric methods or mass spectroscopy linked with controlled thermal decomposition of the organic complex it is possible to determine at what temperature either under calcination conditions or pyrolysis conditions that initial decomposition and total decomposition of the organic complex occurs. This indicates the temperature range at which this partial decomposition stage should be undertaken or the minimum temperature that should be selected of full decomposition is required. Alternatively when analyzed by infrared transmission spectroscopy it may be determined at what point in the treatment that a certain functional group is either removed from or formed in the organic complex; the temperature at which this occurs if below the total decomposition temperature may be selected as the temperature for the partial decomposition or if above the total decomposition temperature may be selected as the temperature for full decomposition. In the case where amines are used as the organic compound the temperature below which significant quantities of nitrogen oxides are produced may be selected as the temperature for treatment to induce partial decomposition. For other organic compounds it may be the temperature at which CO or $CO_2$ are removed from the complex. In the case of amines and especially amines containing hydroxyl groups or amino acids as the organic compound it may be the formation of new vibration bands that appear in the infra-red spectra at between 2100-2200 cm$^{-1}$ and tentatively assignable to complex carbon nitrogen species such as nitrites and isonitriles being present in the partially decomposed organic complex. Another method that may be used is where TGA analysis shows total weight loss of the organic complex; temperatures below total weight loss may be selected for partial decomposition and temperatures at or above the temperature for total weight loss may be selected for full decomposition.

When calcination is used to partially or fully decompose the organic complex the calcination temperatures used are typically within the range of 200 to 1000° C., preferably from 250 to 600° C. The exact temperature used will depend on whether or not full or partial decomposition of the organic complex is desired and will depend on the nature of the organic complex. Factors that may affect the decomposition temperature of the organic metal complex include the nature of the metal and/or organic compound within the complex. Another factor may be the nature of the counter-ion present when the metal is introduced in the form of a salt. Preferably when partial decomposition is required the support with the organic complex deposited thereon is calcined at a temperature that is less than the temperature as determined by TGA in air, at which total weight loss of the organic complex occurs. Preferably it is between 200° C. and the temperature at which total weight loss of the organic complex occurs. Preferably when full decomposition is required the support with the organic complex deposited thereon is calcined at a temperature that is at or above the temperature, as determined by TGA, at which total weight loss of the organic complex occurs. Preferably it is between the temperature at which total weight loss of the organic complex occurs and 1000° C. Under calcination conditions oxygen is present either as a component of an otherwise inert diluent or as a consequence of calcination being undertaken in air. When pyrolysis is used the pyrolysis may be undertaken in an inert atmosphere free of oxygen or in a hydrogen atmosphere that may be and preferably is free of oxygen. When pyrolysis is used the organic complexes may decompose at higher temperatures than those observed under calcinations conditions. As with calcination the temperature, under pyrolysis conditions, for partial or full decomposition may be determined using a variety of methods of which TGA is preferred. Preferably when partial decomposition is required under pyrolysis conditions in an inert atmosphere or under hydrogen, the support with the organic complex deposited thereon is pyrolysed in an inert atmosphere or under hydrogen at a temperature that is less than the temperature as determined by TGA in an inert atmosphere or under hydrogen, at which total weight loss of the organic complex occurs. Preferably it is between 200° C. and the temperature at which total weight loss of the organic complex occurs under pyrolysis conditions in an inert atmosphere or under hydrogen. Preferably when full decomposition is required the supports with the organic complex deposited thereon are pyrolysed at a temperature that is at or above the temperature, as determined by TGA, at which total weight loss of the organic complex occurs under pyrolysis conditions in an inert atmosphere or under hydrogen. Preferably it is the between the temperature, under pyrolysis conditions in an inert atmosphere or under hydrogen, at which total weight loss of the organic complex occurs and 1000° C. Preferably the supports with the organic complex deposited thereon are pyrolysed in nitrogen or hydrogen at a temperature of less than 1000° C. The support comprising organic complex may be calcined or pyrolysed at the partial decomposition temperature for a period of time that is sufficient to ensure the partial decomposition of the organic complex occurs. Typically this will be for a period of at least 20 minutes, preferably at least 30, more preferably at least 45 minutes and most preferably for 1 hour or more. Typically the period of time is 48 hours or less, preferably 24 hours or less and most preferably 12 hours or less. When full decomposition is required the support comprising organic complex may be calcined or pyrolysed at the full decomposition temperature for a period of time that is sufficient to ensure the full decomposition of the organic complex.

If a plurality of active metals are applied to the support and the application is carried out in succession, the support can be dried at from 100 to 150° C. and, if desired, calcined at from 200 to 600° C. after each application or impregnation.

After partial or full decomposition of the complex the partially decomposed or fully decomposed complex is converted to catalytically active metal, i.e., metal is converted into the reducede form. Preferably, the activation is achieved via treatment of the partially or fully decomposed complex under conditions to reduce the partially or fully decomposed complex in the presence of a reductant source. In preferred embodiments the reductant source is a source of hydrogen and/or carbon monoxide. The conversion my be achieved by introduction of the support containing one or more fully or partially decomposed organic complexes into a process designed to use the final catalyst; in this embodiment the conversion occurs under the process conditions or the conditions present in a catalyst regeneration or recycle unit associated with the process. In a preferred embodiment this treatment is undertaken using conditions and methods normally used for the activation of catalysts. These conditions and methods are selected to ensure that the fully or partially decomposed complex catalyst precursor is converted to catalytically active metal. In one embodiment the treatment with reductant, e.g., source of hydrogen and/or CO is carried out by contacting the support comprising partially decomposed complex with a gas stream comprising reductant, e.g., a source of hydrogen and/or CO at from 30 to 600° C., preferably from 100 to 550° C., even more preferably from 200 to 500° C., and most preferably from 200 to 450° C. When the reductant stream comprises free hydrogen it preferably consists of from 50 to 100% by volume of $H_2$ and from 0 to 50% by volume of $N_2$. The treatment may be carried our under a continuous flow of reductant, e.g., source of hydrogen and/or CO under atmospheric pressure or under static conditions at elevated pressures up to 100 bar, preferably 1 to 90 bar, more preferably 1 to 20 bar. The activation may be undertaken for a period of up to 48 hours, preferably no more than 36 hours, more preferably less than 24 hours, and most preferably from 30 minutes to 12 hours. In the case wherein the support comprises a partially decomposed complex, it is exposed to reductant, e.g., source of hydrogen and/or CO at atmospheric pressure and the temperature is raised at a rate of 2° C. min$^{-1}$ to the treatment temperature where reductant treatment is continued for a further 1 to 10 hours, preferably 2 to 8 hours and most preferably 3 to 6 hours. The exact temperature and time are selected to ensure that under the reductant treatment any residual partially decomposed organic complex is removed; therefore the reductant treatment temperature is generally higher than the decomposition temperature of the organic complex and especially of the partially decomposed organic complex. In the case of nickel, for example, it is preferred that the reduction temperature be high enough to convert the organic complex or partially decomposed organic complex of nickel oxide or salt into at lest about 10% reduced metal preferably at least about 12% reduced metal, more preferable at least about 13% reduced metal based on the total weight of the reduced catalyst. An initial reduction at temperature of about 350 to 500° C., preferably about 400° C. for at least about 1 hour is desirable for nickel.

The catalyst samples prepared herein, or those obtained from commercial sources can be used as supplied or can be subjected to an activation procedure to increase the amount of active metal on the catalyst to the reduced or zero valence metal state. These procedures are well established and known by those skilled in the art. In general, an increase in the amount of metal in the reduced or metallic state may correspond with increased catalytic activity. Commercially available catalysts are typically reduced/activated by the manufacturer and passivated before shipment or shipped under oil. The customer can then either use the catalyst as received or perform a separate reactivation step. Depending on the catalytic metal used and the reduction properties of the catalysts used, sufficient metal reduction may take place during catalyst use at the process temperature and hydrogen pressure used so as to make a separate reactivation step unnecessary. If the degree of metal activation at the process conditions is not sufficient, catalyst may be reduced prior to use. If the reduction has to be performed externally to the catalytic reactor, reduction followed by passivation may be performed to allow for aerobic catalyst transfer. In the examples presented, the activation protocol, if any, will be described and the reduced metal content under those conditions will be given as a percentage of the total catalyst composition.

Chemisorption measurements are commonly used to estimate the size of supported metal catalysts and metal surface area. The general method for measuring metal surface area by chemisorption is described in J. Lemaitre et al., "Characterization of Heterogenous Catalysts", edited by Francis Delanney, Marcel Dekker, New York (1984), pp. 310-324. The total metal surface area on the catalyst is preferably from 0.01 to 100 m$^2$/g, particularly preferably from 0.05 to 50 m$^2$/g and more preferably from 0.05 to 25 m$^2$/g of the catalyst. From chemisorption measurements, the % dispersion (% of metal atoms that populate the surface of the metal particles) can be estimated since a properly chosen titrant used in the chemisorption measurements adsorbs only on metal atoms populating the surface. Consequently higher dispersion values indicate smaller particles with more of the metal atoms populating the surface. For many reactions, activity correlates with dispersion. The preferred method for determining metal dispersion is by using hydrogen as the chemisorption probe molecule under high vacuum static conditions as follows. The sample is held at a temperature of 40° C. and an 8-point isotherm (with pressures between 80 and 400 torr) is obtained using H$_2$ as the chemisorption probe molecule. The linear portion of this isotherm is extrapolated to zero pressure to obtain the total quantity of hydrogen chemisorbed; this is the combined dispersion. The sample is then evacuated at 40° C. to remove any weakly adsorbed hydrogen and the titration repeated to determine what is referred to as weak adsorption isotherm. The linear portion of this weak adsorption isotherm is extrapolated to zero pressure to obtain the quantity of weakly chemisorbed hydrogen. Subtraction of these two values for combined dispersion and weak dispersion yields the strongly held chemisorbed quantity. Thus this method provides values for the total metal dispersion, the dispersion due to weakly chemisorbed hydrogen and dispersion due to strongly chemisorbed hydrogen. The value for the strongly chemisorbed hydrogen is an accurate indication of metal dispersion. In many prior art references the metal dispersion figures provided are based on the total chemisorbed probe and are not split into strong and weak components. In the present process it is preferred that the catalysts used have dispersion values relating to the strongly chemisorbed component in excess of 5% more preferably in excess of 10% and most preferably in excess of 15%.

When reference is made to relatively small metal particles as active metal sites it is meant metal particles with an average particle size of 25 nm or less, preferably 15 nm or less, and most preferably 9 nm or less.

In the evaluation of new catalysts for the synthesis of EETB, attention must be paid to both activity and selectivity. Activity is indicated by the degree of conversion of the DEG starting material in a given time period. Selectivity is obtained by comparing the production of the desirable product to that of the by-product at a given conversion of DEG. In the performance of the catalysts in the present invention, a distinct activity advantage was observed. Selectivity toward the desired product was higher at higher conversion than the current state of the art catalysts (i.e., less by-product formation at increased conversion levels). Selectivity and activity are important in the commercial operation because conversion in commercial production can be limited as a consequence of the production of TBM by-product, to low levels of conversion of DEG. For the present catalyst, the level of DEG conversion is higher than that of the prior catalysts with high levels of EETB production at high EETB/TBM ratios.

In the examples, except where otherwise indicated, the data presented in the tables were obtained by using the normalized weight percent values of all products and all reactants from the GC. The conversion was calculated by following method: the concentration of DEG as charged minus the DEG concentration at the time point of interest, this quantity divided by the DEG concentration as charged and multiplied by 100 to give a percent DEG converted. Note that one mole of DEG reacts with one mole of TBA to form one mole EETB and normalizing on the basis of DEG conversion takes this into account. In some of the examples, the % DEG converted is reported as negative. This occurs for low activity catalysts, and is an artifact of the normalization of the sample and volatilization of the TBA upon sampling at high temperature. The GC reports the relative concentration of each reactant and product component in the entire sample. Because small amounts of TBA are evaporated, the relative amount of DEG in the sample is reported to be higher. When compared with the initial concentration at the reactor loading, the DEG appears to have increased in concentration. The conversion values were reported as calculated, and although they are reported as negative, they should effectively be considered zero conversion. This tendency would also occur to some extent in the other calculations of conversion, thus these numbers likely represent a lower bound on conversion, but should occur to the same degree in all the samples and a meaningful comparison between runs can be made. The weight percent ratios for the EETB/TBM and EETB/Bis-SE ratios were obtained by simply taking the ratio of the respective weight percents from the GC trace. The molar ratios were determined by converting the ratio from grams/grams to moles/moles by dividing the weigh percent of each component by its molecular weight.

In some of the examples, catalyst samples were charged into the autoclave as received and used without hydrogen re-activation. In those cases, the reduced Ni content in the catalyst was estimated by TGA measurement of the reduced metal content in the catalyst after one-hour reduction in hydrogen at 200° C. This is believed to be a close approximation of the degree of reduction taking place in the autoclave after it is charged, pressurized with hydrogen and brought to the reaction temperature.

EXAMPLES

Example 1

Preparation of 19.5% Ni on MCM-41/Alumina Bound with TEA Additive in the Solution 15.0 g of alumina bound MCM-41 extrudate support (whereby MCM-41 is an ordered silicous mesoporous material and alumina is the matrix.) was impregnated to the incipient wetness point with a solution prepared by dissolving 19.28 g of nickel nitrate hexahydrate in 6.82 g of water and 2.47 g of triethanolamine. The sample was then dried in air at 100° C. for four hours. The dried sample was calcined in flowing air by gradually ramping the temperature according to the following protocol to temper the vigorous oxidation reaction between nickel nitrate and the amino alcohol: 2° C./minute to 140° C. and hold for 30 minutes, 1° C./minute to 175° C. and hold for 30 minutes. The catalyst was then activated by reduction at 400° C. in flowing hydrogen (200 cc/min $H_2$ and 50 cc/min $N_2$) for 1 hour at atmospheric pressure according to the following protocol: heat in flowing hydrogen at 2° C./min from room temperature to 400° C. and hold at 400° C. for 1 hour. The so reduced catalyst was passivated to permit aerobic transfer to the autoclave for testing. Passivation was accomplished by cooling the reduced catalyst to room temperature under hydrogen flow. When cooled, the hydrogen was replaced by nitrogen and the catalyst was purged in nitrogen for an hour and gradually exposed to increasing concentrations of oxygen in nitrogen diluent. First, 0.02% oxygen in nitrogen was used for 30 minutes, followed by 0.1% oxygen in nitrogen for 30 minutes, followed by 0.3% oxygen in nitrogen for 30 minutes, followed by 10% oxygen in nitrogen for 30 minutes, and finally followed by 20% oxygen in nitrogen for 30 minutes.

Example 2

Synthesis of EETB 1.59 g of Ni (19.5%) on alumina bound MCM-41, the material of Example 1, (crushed into a powder) was employed to synthesize EETB.

Prior to use, the catalyst was re-activated at 200° C./1 psi of hydrogen at 50 cc/min for 18 hours in-situ resulting in about 14% reduced nickel metal based on the whole reduced catalyst. 108.0 g of tertiary-butyl amine and 76.4 g of diethylene glycol, a 2:1 mole ratio of TBA:DEG, were then charged to the reactor under nitrogen at room temperature. The contents of the autoclave reactor were heated at 180° C. and stirred at 1800 rpm for 6 hours with GC sampling at hourly intervals. Reactor temperature was held at 180° C. Initial hydrogen pressure at room temperature was 100 psig, total reactor pressure at 180° C. was 372 psig.

The results are presented below:

| Time | Products (GC Weight %) | | | | DEG Conv | EETB/TBM | EETB/TBM | EETB/Bis SE | EETB/Bis SE |
|---|---|---|---|---|---|---|---|---|---|
| (h) | Bis-SE[2] | EETB | TBM[1] | DEG | (%) | (wt) | (molar) | (wt) | (molar) |
| 1 | 0.01 | 3.1 | 0.03 | 38.0 | 5.2 | 117.8 | 105 | 314.2 | 421.5 |
| 2 | 0.03 | 6.7 | 0.1 | 37.5 | 6.6 | 89.6 | 80 | 220.8 | 296.2 |
| 3 | 0.1 | 10.3 | 0.2 | 36.6 | 8.8 | 67.9 | 60 | 166.9 | 223.9 |
| 4 | 0.1 | 12.5 | 0.2 | 32.9 | 18.0 | 53.9 | 48 | 125.4 | 168.3 |
| 5 | 0.2 | 17.0 | 0.4 | 30.1 | 25.1 | 41.3 | 37 | 84.2 | 112.9 |
| 6 | 0.3 | 22.0 | 0.6 | 30.6 | 23.8 | 39.2 | 35 | 65.2 | 87.5 |

[1]TBM is N-tertiary-butylmorpholine, an undesirable by-product
[2]Bis-SE is 2,2'-tertiary-butylamino ethyl ether, or bis(tertiary butylaminoethoxy) ethane After 6 hours the mole ratio of EETB/TBM produced was 35 at 24% conversion of diethylene glycol. The mole ratio of EETB/TBM is a convention used to compare selectivity of the catalysts being evaluated. It essentially describes how many moles of EETB are produced per mole TBM at a given conversion. The higher the EETB/TBM mole ratio, the more selective the catalyst.

Example 3

Synthesis of EETB

The procedure of Example 2 was repeated but using 107.0 g of tertiary-butyl amine and 75.6 g of diethylene glycol (2:1 mole ratio). The catalyst was the catalyst of Example 2, re-activated at 200° C., 1 psi of hydrogen at 50 cc/min flow rate for 18 hours in-situ. The catalyst is about 14% reduced nickel metal based on the whole reduced catalyst. Reactor temperature was held at 200° C. with stirring at 1800 rpm for 7 hours and the total reactor pressure was 385 psig. Initial hydrogen pressure at room temperature was 100 psig.

The results are presented below:

Results of Example 3.

| Time (h) | Products (GC Weight %) | | | | DEG Conv (%) | EETB/TBM (wt) | EETB/TBM (molar) | EETB/Bis SE (wt) | EETB/Bis SE (molar) |
|---|---|---|---|---|---|---|---|---|---|
| | Bis-SE | EETB | TBM | DEG | | | | | |
| 0.75 | 0.02 | 9.8 | 0.05 | 30.5 | 23.9 | 207.3 | 184 | 456.2 | 612.0 |
| 2 | 0.1 | 12.3 | 0.1 | 31.4 | 21.6 | 93.0 | 83 | 192.0 | 257.6 |
| 3 | 0.2 | 20.1 | 0.3 | 29.1 | 27.5 | 63.1 | 56 | 107.6 | 144.4 |
| 4.4 | 0.4 | 26.1 | 0.8 | 22.0 | 45.2 | 34.1 | 30 | 62.8 | 84.3 |
| 5.6 | 0.9 | 37.2 | 1.2 | 23.3 | 41.8 | 31.0 | 28 | 43.1 | 57.8 |
| 6 | 0.8 | 31.6 | 1.5 | 16.9 | 57.9 | 21.4 | 19 | 37.9 | 50.9 |
| 8 | 1.4 | 38.3 | 2.3 | 15.0 | 62.5 | 16.5 | 15 | 26.9 | 36.1 |

After 6 hours at 200° C. the mole ratio of EETB/TBM was 19 at 57.9% diethylene glycol conversion. Comparing Example 3 with Example 2, it is apparent that higher temperature operation increases conversion significantly.

Comparative Examples

Two prior art catalysts were run for comparison purposes for the synthesis of EETB.

Comparative Example A

E480-P is a nickel catalyst containing about 65% nickel deposited on a support. It has an average particle diameter of 9 μm, and an apparent bulk density of 20 lbs/ft$^3$.

Comparative Example B

EETB synthesis procedures similar to those used in Example 1 were employed.

A fresh sample of E 480-P (Comparative Example A) was evaluated at 180° C. for EETB synthesis. The catalyst was re-activated before use at 200° C. in 1 psi of hydrogen at 50 cc/min for 19 hours resulting in a metallic reduced nickel content of about 53% based on the whole reduced catalyst. 108.0 g of TBA and 76.4 g of DEG (2:1 mole ratio) were charged to an autoclave under nitrogen at room temperature. 1.57 g of catalyst was added. Initial hydrogen pressure at room temperature was 100 psig. The autoclave was heated to 180° C. and the contents stirred at 1800 rpm for 6 hours. Total vessel pressure was 262 psig. Results are presented below.

Results of Comparative Example B. (180° C.)

| Fraction # | Time (h) | Products (GC Weight %) | | | | DEG Conv (%) | EETB/TBM (wt) | EETB/TBM (molar) | EETB/Bis SE (wt) | EETB/Bis SE (molar) |
|---|---|---|---|---|---|---|---|---|---|---|
| | | Bis-SE | EETB | TBM | DEG | | | | | |
| 21-1 | 1 | 0.04 | 5.4 | 0.1 | 41.2 | -2.7 | 83.1 | 74 | 144.2 | 193.5 |
| 21-2 | 2 | 0.05 | 10.6 | 0.2 | 40.7 | -1.5 | 68.3 | 61 | 219.0 | 293.8 |
| 21-3 | 3 | 0.1 | 13.5 | 0.3 | 34.4 | 14.3 | 47.6 | 42 | 105.8 | 142.0 |
| 21-4 | 4 | 0.2 | 18.8 | 0.6 | 28.9 | 27.9 | 31.1 | 28 | 78.2 | 104.9 |
| 21-5 | 6 | 0.5 | 27.5 | 1.5 | 26.1 | 34.9 | 18.8 | 17 | 59.7 | 80.1 |

Comparative Example C

A fresh sample of catalyst E 480-P was employed. It was not reactivated before evaluation in this example. Earlier work had shown that this commercial catalyst performed similarly whether reactivated or used as received. About 107.8 g of TBA and 76.2 g of DEG (2:1 mole ratio) were charged to an autoclave under nitrogen at room temperature. 1.59 g of catalyst was. added. Initial hydrogen pressure at room temperature was 100 psig. The autoclave was heated to 200° C. and the contents stirred at 1800 rpm for 7 hours. Based on reduction experiments done on this catalyst at 200° C. for 1 hour in hydrogen, it is believed that reduction occurs in the course of use in the process run at 200° C. in hydrogen, the reduced metal content is believed to be about 47-48% nickel based on the whole reduced catalyst. Total vessel pressure was 385 psig. Results are presented below.

Results of Comparative Example C. (200° C.)

| Fraction # | Time (h) | Products (GC Weight %) | | | | DEG Conv (%) | EETB/TBM (wt) | EETB/TBM (molar) | EETB/Bis SE (wt) | EETB/Bis SE (molar) |
|---|---|---|---|---|---|---|---|---|---|---|
| | | Bis-SE | EETB | TBM | DEG | | | | | |
| 32-1 | 1 | 0 | 2.8 | 0.02 | 43.3 | −7.5 | 134.7 | 120 | | |
| 32-2 | 2 | 0.02 | 7.3 | 0.06 | 51.5 | −28.3 | 115.0 | 102 | 324.1 | 434.8 |
| 32-3 | 3 | 0.05 | 10.8 | 0.1 | 47.9 | −19.5 | 87.8 | 78 | 238.8 | 320.3 |
| 32-4 | 4 | 0.1 | 16.5 | 0.3 | 44.2 | −10.3 | 59.4 | 53 | 168.6 | 226.2 |
| 32-5 | 5 | 0.2 | 22.5 | 0.6 | 36.5 | 9.1 | 37.9 | 34 | 114.1 | 153.0 |
| 32-6 | 6 | 0.3 | 27.0 | 1.0 | 31.3 | 31.9 | 28.4 | 25 | 86.3 | 115.8 |
| 32-7 | 7 | 0.4 | 27.1 | 1.2 | 25.6 | 36.1 | 21.8 | 19 | 73.4 | 98.5 |

E-480P is not only less active than the catalyst in Example 3, but its selectivity toward EETB is significantly lower both at the same and even at higher DEG conversion levels than the catalyst described in Example 3.

Comparative Example D 1.14 g of E 480-P (Comparative Example A) was employed to synthesize EETB. The catalyst was used as received. 66.0 g of tertiary-butyl amine, 47.9 g of diethylene glycol, and 119.0 grams of toluene (as an inert solvent) were then charged to the reactor under nitrogen at room temperature. The autoclave was charged at room temperature with 100 psig of hydrogen. The contents of the autoclave reactor were then heated to 200° C. and stirred at 1800 rpm for 6 hours. Based on reduction experiments done on this catalyst at 200° C. for 1 hour in hydrogen, it is believed the reduced metal content is about 47-48% based on the whole reduced catalyst, see Comparative Example C, such reduction occurring in the course of the use of the catalyst in the process run at 200° C. in hydrogen. The total reactor pressure at 200° C. was 310 psig. The final reactor product was analyzed by NMR. The results are presented below.

Results of Comparative Example D

| Time | Products (¹H NMR) | | | EETB/TBM | % Conversion |
|---|---|---|---|---|---|
| (h) | EETB | TBM | DEG | Mole ratio | Based on DEG |
| 6 | 50 | 6 | 44 | 8 | 56 |

Comparative Example E

Ni 5132-P is a nickel catalyst containing about 60% nickel deposited on a support. It has a surface area of about 160 m²/g, an average particle size of about 6 μm and a pore volume of about 0.00508 ml/g.

Comparative Example F 1.11 g of Ni-5 132-P (Comparative Example E) was employed to synthesize EETB. The catalyst was used as received. 66.0 g of tertiary-butyl amine, 47.9 g of diethylene glycol, and 119.0 g of toluene (as inert solvent) were then charged to the reactor under nitrogen at room temperature. The autoclave was charged at room temperature with 100 psig of hydrogen. The contents of the autoclave reactor were then heated to 200° C. and the contents stirred at 1800 rpm for 6 hours. Based on reduction experiments done on this catalyst at 200° C. for 1 hour in hydrogen, it is believed the reduced metal content is about 52% based on the whole rediced catalyst, in this case the reduction occurring in-situ during the process step. The pressure at 200° C. was 290 psig. The final reactor product was analyzed by NMR. The results are presented below.

Results of Comparative Example F

| Time | Products (¹H NMR) | | | EETB/TBM | % Conversion |
|---|---|---|---|---|---|
| (h) | EETB | TBM | DEG | Mole ratio | Based on DEG |
| 6 | 72 | 15 | 13 | 5 | 87 |

Comparative Examples D and F show that the two prior art catalysts run under the same conditions have lower selectivity than the catalyst of Example 1.

Comparative Example G

The catalyst of Comparative Example E was evaluated in another run for the synthesis of EETB 109.5 g of TBA and 77.6 g of DEG were loaded into an autoclave reactor at room temperature under nitrogen. 1.61 g of the catalyst of Comparative Example E was added as received from the supplier to the reactor. Initial hydrogen pressure at room temperature was 100 psig. Reactor contents were heated at 200° C. and stirred at 1800 rpm for 4 hours with GC sampling every hour. Based upon reduction experiments done on this catalyst at 200° C. for 1 hour in hydrogen, it is believed the reduced nickel content is about 52% based on the whole reduced catalyst, in this case the reduction occurring in-situ during the process step. Total reactor pressure at reaction temperature was 385 psi. The results are presented below.

| Fraction # | Time (hours) | DEG Conv (%) | EETB/TBM (wt) | EETB/TBM (molar) | EETB/BIS SE (wt) | EETB/Bis SE (molar) |
|---|---|---|---|---|---|---|
| 51-1 | 1 | 18.8 | 57.6 | 51 | 1.1 | 1.5 |
| 51-2 | 2 | 45.1 | 25.7 | 23 | 0.8 | 1.1 |
| 51-3 | 3 | 53.0 | 16.8 | 15 | 0.7 | 0.9 |
| 51-4 | 4 | 65.1 | 11.0 | 11 | 0.7 | 0.9 |

Comparative Example H

Preparation of 19.5% Ni on MCM-41 without TEA additive in the solution 5.0 g of alumina bound MCM-41 extrudate support (whereby MCM-41 is an ordered siliceous mesoporous material and alumina is the matrix) was impregnated to the incipient wetness point with a solution prepared by dissolving 6.44 g of nickel nitrate hexahydrate in 2.10 g of water. The sample was then dried in air at 60° C. for 2 hours and at 100° C. for 2 hours. The dried sample was calcined in flowing air by gradually ramping the temperature according to the following protocol: 1° C./minute to 205° C. and hold for two hours, 1° C./minute to 300° C. and hold for two hours. The catalyst was then activated by reduction at 400° C. in flowing hydrogen (200 cc/min $H_2$ and 50 cc/min $N_2$) for 1 hour according to the following protocol: heat is flowing hydrogen at 2° C./min from room temperature to 400° C. for 1 hour. The so reduced catalyst was passivated to permit aerobic transfer to the autoclave for testing. Passivation was accomplished by cooling the reduced catalyst to room temperature under hydrogen flow. When cooled, the hydrogen was replaced by nitrogen and the catalyst was purged in nitrogen for an hour and gradually exposed to increasing concentrations of oxygen in nitrogen diluent. First 0.02% oxygen in nitrogen was used for 30 minutes, followed by 0.1% oxygen in nitrogen for 30 minutes, followed by 0.3% oxygen in nitrogen for 30 minutes, followed by 10% oxygen in nitrogen for 30 minutes and finally followed by 20% oxygen in nitrogen for 30 minutes.

Comparative Example I 107.8 g of TBA and 78.0 g of DEG (2:1 molar ratio) were charged to an autoclave at room temperature under nitrogen. 1.60 g of the catalyst of Example H was reactivated at 200° C./1 psi of $H_2$ flow at 50 cc/min for 18 hours in the reactor before the addition of the TBA/DEG mixture resulting in about 17% reduced nickel metal based on the whole reduced catalyst. Starting hydrogen pressure at room temperature was 100 psig. The reactor contents were stirred at 1800 rpm and heated at 200° C. for 8 hours with GC at the times indicated below. The results are presented below:

| | Ni on MCM-41/alumina bound AM02 30-2 (without TEA additive), 200° C. | | | | | | |
|---|---|---|---|---|---|---|---|
| Fraction # | Time (hrs) | Pressure (psi) | DEG Conv (%) | EETB/TBM (wt) | EETB/TBM (molar) | EETB/Bis SE (wt) | EETB/Bis SE (molar) |
| 52-1 | 1 | 383 | 2.1 | 101.3 | 90 | | |
| 52-2 | 2 | 370 | 5.8 | 87.8 | 78 | 1.3 | 1.7 |
| 52-3 | 3 | 372 | 8.5 | 81.6 | 72 | 2.3 | 3.0 |
| 52-4 | 4 | 370 | 15.3 | 69.8 | 62 | 2.0 | 2.7 |
| 52-5 | 5 | 369 | 15.0 | 66.5 | 59 | 2.0 | 2.6 |
| 52-6 | 8 | 364 | 18.5 | 57.3 | 51 | 1.6 | 2.2 |

Figure 1:
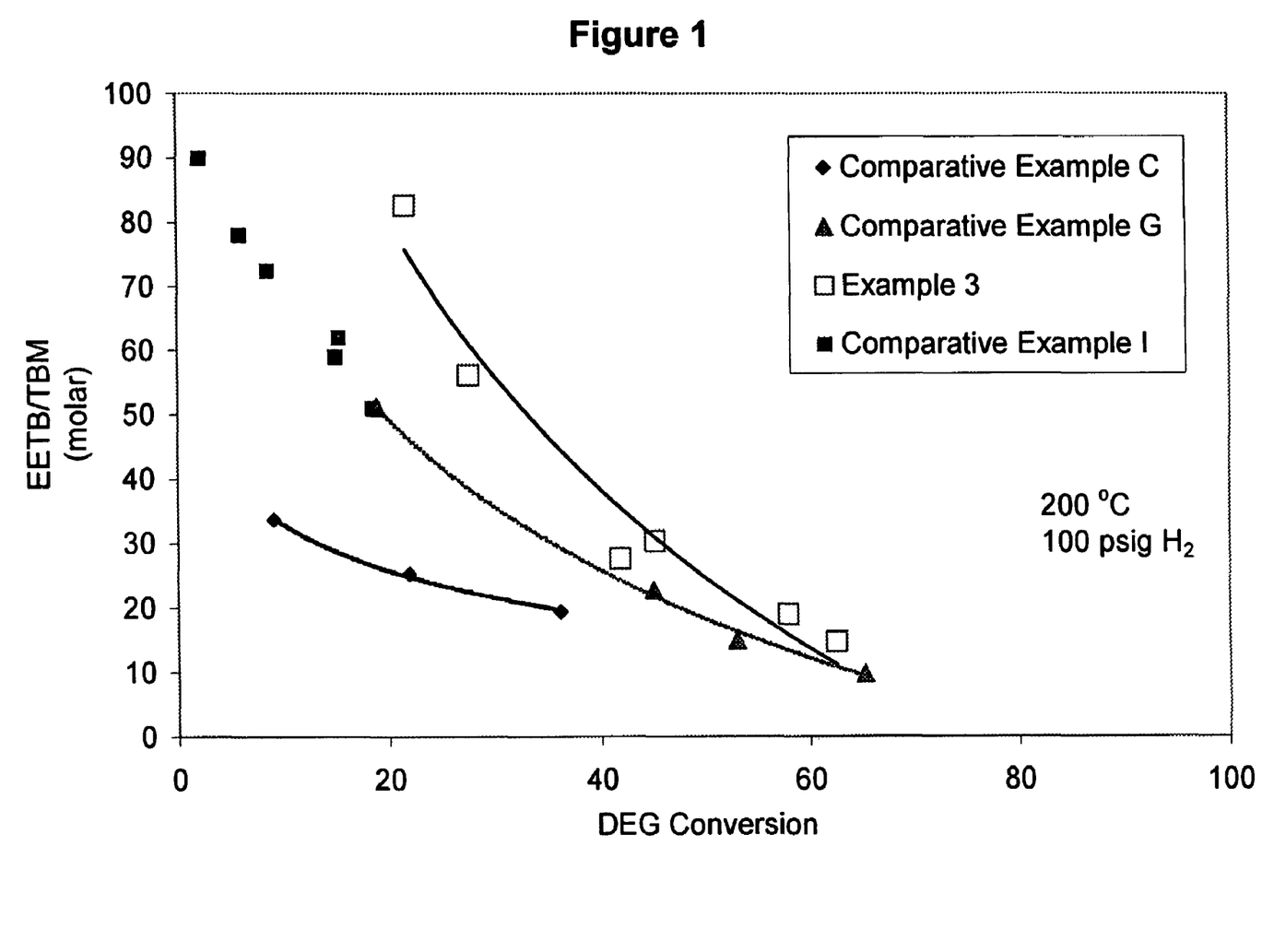
FIG. 1 is a plot of the level of diethylene glycol conversion versus the EETB/TBM molar ratio for a process run using a catalyst made using an organic dispersion aid and representative of those useable in the present invention as compared against three other process runs which utilize catalysts made without the use of an organic dispersion aid and representative of those outside the present invention. TBM is an undesirable side product (N-tertiary-butylmorpholine).

FIG. 1 compares the data for Example 3, Comparative Example C, Comparative Example G and Comparative Example I. It is clear from the figure that the catalyst of Example 3, made using TEA dispersion aid is markedly superior in performance based on the EETB/TBM ratio and degree of DEG conversion at comparable time periods. Example 3 shows that a higher degree of DEG conversion is obtained at a high EETB/TBM ratio than any of the other examples using different catalysts. Example 3 achieves the superior result at a reduced nickel loading of about 14% reduced nickel. This is to be compared against Comparative Examples C and G which utilize catalysts with about 47-48% and 52%, respectively, of reduced nickel based on the whole reduced catalyst. Thus, catalyst of Example 3 achieves equivalent to somewhat superior results at an about 70% lower active metal content. Comparing Example 3 against Comparative Example I it is seen that the process utilizing the catalyst made using an organic dispersion aid (CIEA) achieves superior results in terms of EETB/TBM ratio versus DEG conversion. Example 3 is marked by higher levels of DEG conversion at comparable time periods to Comparative Example I. This higher level of DEG conversion is accompanied by a higher EETB/TBM ratio, indicating that more of the desirable EETB product is produced in Example 3.

Comparative Examples J and K

Two additional catalysts were evaluated for EETB production. One contained 1.2% platinum on MCM-41/$SiO_2$ base (14×25 mesh), the other contained 0.9% palladium/0.3% platinum on MCM-41/$Al_2O_3$. Both catalysts employed the metal in the dispersed form. Metals were in a dispersed form by a technique other than the one described in this case.

In both instances 108.0 g of TBA and 76.4 g of DEG (2:1 mole ratio) were charged to an autoclave reactor under nitrogen at room temperature. 1.59 g of catalyst was added. The catalysts were each activated at 200° C. in 1 psi of hydrogen at a hydrogen flow of 50 cc/min for 19 hours. Initial hydrogen pressure at room temperature in the autoclave was 100 psig. The autoclave was heated to 180° C. and stirred at 1800 rpm for 6 hours and GC samples were taken at the intervals indicated. The results are presented below.

| | | Platinum on MCM-41/SiO$_2$ | | | |
|---|---|---|---|---|---|
| | | MCM-41/SiO2 Pt at 180° C. (100 psig of H$_2$, 2:1 TBA/DEG) | | | |
| Fraction # | Time (hrs) | DEG Conv (%) | EETB/ TBM (wt) | EETB/ TBM (molar) | EETB/Bis SE (wt) | EETB/Bis SE (molar) |
| 23-1 | 1 | 6.0 | 6.7 | 6 | NA | NA |
| 23-2 | 2 | 2.4 | 9.1 | 8 | NA | NA |
| 23-3 | 3 | 5.7 | 10.1 | 9 | NA | NA |
| 23-4 | 6 | 0.6 | 10.4 | 9 | NA | NA |

| | | Palladium/Platinum on MCM-41/Al$_2$O$_3$ | | | |
|---|---|---|---|---|---|
| | | 0.9% Pd/0.3% Pt MCM-41/Al$_2$O$_3$, 180° C. | | | |
| Fraction # | Time (hrs) | DEG Conv (%) | EETB/ TB (wt) | EETB/ TBM (molar) | EETB/Bis SE (wt) | EETB/Bis SE (molar) |
| 25-1 | 1 | 0.0 | 15.3 | 14 | NA | NA |
| 25-2 | 3 | 3.1 | 14.6 | 13 | 143.8 | 192.9 |
| 25-3 | 5 | 3.1 | 14.4 | 13 | 93.7 | 125.7 |
| 25-4 | 6 | 1.7 | 15.4 | 14 | 85.1 | 114.1 |

As can be seen, platinum and palladium metal loaded MCM-41 does not function as a good EETB synthesis catalyst.

Example 4

Preparation of 29.8% Ni on SiO$_2$ with TEA Additive in the Solution 25.0 g of a conventional amorphous (an amorphous mesoporous material) silica support (250 m$^2$/g) was impregnated to the incipient wetness point with solution prepared by dissolving 58.40 g of nickel nitrate hexahydrate in 20.68 g of water and 7.48 g of triethanolamine. The sample was then dried in air at 100° C. overnight. The dried sample was calcined in flowing air by gradually ramping the temperature according to the following protocol to temper the vigorous oxidation reaction between nickel nitrate and the aminoalcohol: 2° C./minute to 160° C. and hold for 30 minutes, 1° C./minute to 185° C. and hold for 30 minutes, 1° C./minute to 215° C. and hold for 30 minutes, 1° C./minute to 300° C. and hold for one hour. A 27.00 g sample of the thus prepared material was re-impregnated to incipient wetness point with solution prepared by dissolving 25.18 g of nickel nitrate hexahydrate in 8.92 g of water and 3.23 g of triethanolamine. The sample was then dried in air at 100° C. for four hours. The dried sample was calcined in flowing air by gradually ramping the temperature according to the following protocol: 1° C./minute to 150° C. and hold for one hour, 1° C./minute to 300° C. and hold for one hour.

Example 5

Synthesis of EETB Using Dispersed Nickel Loaded SiO$_2$ 1.59 g Ni on 250 m$^2$/g silica (150 Å pore) (29.8% nickel) was employed to synthesize EETB.

The catalyst was prepared prior to use by activating at 200° C. in 1 psi of hydrogen flow at 50 cc/minute for 13 hours before being charged to an autoclave reactor resulting in about 23% reduced nickel metal based on the whole reduced catalyst. 108.0 g of TBA and 76.4 g of diethylene glycol (DEG) (2:1 molar ratio) were charged to the reactor under nitrogen at room temperature. Initial hydrogen pressure in the autoclave at room temperature was 100 psig. The contents of the autoclave were heated at 180° C. with stirring at 1800 rpm for 8 hours with GC sampling at the times indicated. Total reactor pressure at reaction temperature was 253 psig. The results are presented below:

| | | Ni on 250 m2/g silica (150A pore) (AM02-69-4), 180° C. | | | |
|---|---|---|---|---|---|
| Fraction # | Time (hrs) | DEG Conv (%) | EETB/ TBM (wt) | EETB/ TBM (molar) | EETB/Bis SE (wt) | EETB/Bis SE (molar) |
| 29-1 | 1 | −24.4 | 16.0 | 14 | 1.6 | 2.1 |
| 29-2 | 2 | −7.4 | 13.4 | 12 | 2.4 | 3.3 |
| 29-3 | 3 | −15.5 | 29.6 | 26 | 0.7 | 1.0 |
| 29-4 | 4 | −29.4 | 38.8 | 34 | 3.0 | 4.1 |
| 29-5 | 5 | −21.4 | 30.9 | 27 | 4.4 | 5.9 |

Example 6

The procedure of Example 5 was repeated, but in this instance the catalyst was reduced at 400° C. and passivated using the procedure recited in Example 1. The catalyst was re-activated at 200° C. in 1 psi of hydrogen flow at 50 cc/min for 13 hours before use. The catalyst was about 28% reduced nickel metal based on the whole reduced catalyst. Reactor temperature was again held at 180° C. with stirring at 1800 rpm for 8 hours with GC sampling at the times indicated below. Initial hydrogen pressure at room temperature was 100 psig. Total reactor pressure at reaction temperature was 253 psig. The results are presented below.

| | | Ni on 250 m2/g silica (150A pore) (AM02-69-5), 180° C. | | | |
|---|---|---|---|---|---|
| Fraction # | Time (hrs) | DEG Conv (%) | EETB/ TBM (wt) | EETB/ TBM (molar) | EETB/Bis SE (wt) | EETB/Bis SE (molar) |
| 28-1 | 1 | 7.6 | 108.0 | 96 | 1.3 | 1.7 |
| 28-2 | 2 | 17.7 | 67.2 | 60 | 0.8 | 1.1 |
| 28-3 | 3 | 20.4 | 42.9 | 38 | 0.6 | 0.8 |
| 28-4 | 4 | 24.3 | 31.3 | 28 | 0.6 | 0.7 |
| 28-5 | 5 | 31.6 | 26.5 | 24 | 0.5 | 0.6 |
| 28-6 | 6 | 37.7 | 20.1 | 18 | 0.5 | 0.7 |
| 28-7 | 8 | 53.1 | 14.1 | 13 | 0.5 | 0.7 |

Comparing Example 5 with Example 6 it is seen that reduction at a high enough temperature to insure that the metal is in the active/reduced form is essential for successful practice of the present process.

Comparative Example L 15.0 g of a silica support (250 m²/g) was impregnated to the incipient wetness point with solution prepared by dissolving 19.24 g of nickel nitrate hexahydrate in 6.26 g of water. The sample was then dried in air at 60° C. for 2 hours, then at 100° C. for 1 hour and at 120° C. for 2 hours. The dried sample was calcined in flowing air by gradually ramping the temperature according to the following protocol: 1° C./minute to 205° C. and hold for two hours, 1° C./minute to 300° C. and hold for two hours. The catalyst was reduced at 400° C. in flowing hydrogen for 1 hour (200 cc/hr $H_2$ and 50 cc/hr $N_2$) using the previously described protocol. The so reduced catalyst was passivated to permit aerobic transfer to the autoclave for testing. Passivation was accomplished by cooling the reduced catalyst to room temperature under hydrogen flow. When cooled, the hydrogen was replaced by nitrogen and the catalyst was purged in nitrogen for an hour and gradually exposed to increasing concentrations of oxygen in nitrogen diluent. First, 0.02% oxygen in nitrogen was used for 30 min., followed by 0.1% oxygen in nitrogen for 30 min., followed by 0.3% oxygen in nitrogen for 30 min., followed by 10% oxygen in nitrogen for 30 min. and finally followed by 20% oxygen in nitrogen for 30 min.

Comparative Example M 1.57 g of the catalyst of Comparative Example L was activated at 200° C. in 1 psi of hydrogen flow at 50 cc/min. for 18 hours, in situ, in an autoclave reactor resulting in about 16% reduced nickel metal based on the whole reduced catalyst. 106.0 g of TBA and 76.7 g of DEG (2:1 mole ratio) were added to the autoclave reactor at room temperature under nitrogen. Initial hydrogen pressure at room temperature was 100 psig. Reactor contents were heated at 200° C. with stirring at 1800 rpm for 8 hours with GC sampling at the times indicated below. Total reactor pressure at temperature was 383 psig. The results are presented below.

AM03-29-2: Ni on SiO2, without TEA additive, 200° C.

| Fraction # | Time (hrs) | Pressure (psig) | DEG Conv (%) | EETB/TBM (wt) | EETB/TBM (molar) | EETB/Bis SE (wt) | EETB/Bis SE (molar) |
|---|---|---|---|---|---|---|---|
| 54-1 | 1 | 379 | 8.2 | 111.2 | 98.8 | 2.2 | 2.9 |
| 54-2 | 2 | 370 | 3.8 | 76.1 | 67.6 | 3.9 | 5.3 |
| 54-3 | 3 | 366 | 10.7 | 63.6 | 56.5 | 1.8 | 2.4 |
| 54-4 | 4 | 363 | 7.4 | 60.1 | 53.3 | 2.1 | 2.8 |
| 54-5 | 5 | 355 | 10.0 | 52.9 | 47.0 | 1.7 | 2.3 |
| 54-6 | 8 | 355 | 23.2 | 39.6 | 35.2 | 1.5 | 2.0 |

As can be seen, the process employing the catalyst made using the organic dispersion aid (Example 6) is markedly superior in terms of conversion level achieved in the same reaction time to the process using the nominally same catalyst, but which was made not using the organic dispersion aid (Comparative Example M).

Comparative Example N

The process of Example 2 was repeated, but in this instance the catalyst, Ni MCM-41 was not subjected to a 400° C. activation in hydrogen followed by passivation. Rather, the catalyst was subjected simply to a 200° C. activation step resulting in about 9% reduced nickel metal based on the whole reduced catalyst. The synthesis reaction was conducted at 180° C., 100 psig $H_2$ as per Example 2. The example exhibited minimal DEG conversion and an unmeasurably small EETB production showing that activation at a temperature high enough to secure an active nickel catalyst having at least 10% reduced metal based on the whole reduced catalyst is preferred.

The invention claimed is:

1. A method for synthesizing severely sterically hindered amino ether alcohols, diaminopolyalkenyl ether, and mixtures thereof, by reacting a primary amino compound with a polyalkylene glycol at elevated temperature and pressure in the presence of a catalyst comprising a catalytically active reduced metal excluding platinum and palladium dispersed on a support, the dispersed metal containing catalyst being prepared by a process comprising introducing onto the support one or more organic complexes of one or more catalytic metals, decomposing the one or more organic metal complexes on the support and converting the one or more decomposed organic metal complexes into catalytically active reduced metal.

2. The method of claim 1 wherein the organic complex of one or more catalytic metals is introduced onto the support in the form of a mixture of an organic compound mixed with a compound or salt of one or more catalytic metals.

3. The method of claim 1 wherein the organic complex of one or more catalytic metals is introduced onto the support by treating the support with one or more organic compounds followed by treating the support with one or more organic compounds followed by treating the support containing the one of more organic compounds with one or more compounds or salts of one or more catalytic metals to form the one or more organic complexes of one or more catalytic metals.

4. The method of claim 1 wherein the organic complex of one or more catalytic metals is introduced onto the support by treating the support with one or more compounds or salts of one or more catalytic metals followed by treating the support containing the one or more compounds or salts of one or more catalytic metals with one or more organic compounds to form the one or more organic complexes of one or more catalytic metals.

5. The method of claim 1 wherein the organic complex of one or more catalytic metals is introduced onto the support by treating the support simultaneously with one or more compounds or salts of one or more catalytic metals and one or more organic compounds to form the one or more organic complexes of one or more catalytic metals.

6. The method of claims 1, 2, 3, 4 or 5 wherein the decomposition is a partial decomposition.

7. The method of claims 1, 2, 3, 4 or 5 wherein the decomposition is a complete decomposition.

8. The method of claims 1, 2, 3, 4 or 5 wherein the support comprises one or more mesoporous materials.

9. The method of claims 1, 2, 3, 4 or 5 wherein the support comprises one or more ordered mesoporous materials.

10. The method of claims 1, 2, 3, 4 or 5 wherein the support comprises one or more mixed porosity materials.

11. The method of claims 1, 2, 3, 4 or 5 wherein the support comprises a support selected from the group consisting of one or more conventional amorphous materials, one or more crystalline support materials, and mixtures thereof.

12. The method of claims 1, 2, 3, 4 or 5 wherein the support comprises one or more mesoporous support materials combined with one or more mixed porosity support materials.

13. The method of claims 1, 2, 3, 4 or 5 wherein the support comprises one or more ordered mesoporous support materials combined with one or more mixed porosity support materials.

14. The method of claims 1, 2, 3, 4 or 5 wherein the support comprises one or more mesoporous support materials combined with one or more additional materials selected from the group consisting of conventional amorphous materials crystalline materials and mixtures thereof.

15. The method of claims 1, 2, 3, 4 or 5 wherein the support comprises one or more ordered mesoporous support materials combined with one or more additional materials selected from the group consisting of conventional amorphous materials, crystalline materials, and mixtures thereof.

16. The method of claim 9 wherein the mesoporous support material comprises one or more materials designated as M41S.

17. The method of claim 16 wherein the mesoporous material is MCM-41.

18. The method of claim 11 wherein the support material comprises support materials selected from the group consisting of activated carbon, silicon carbide, aluminum oxide, silicon dioxide, titanium dioxide, zirconium dioxide, magnesium oxide, zinc oxide, and mixtures thereof.

19. The method of claim 18 wherein the support material is selected from the group consisting of aluminum oxide, silicon dioxide, and mixtures thereof.

20. The method of claims 1, 2, 3, 4 or 5 wherein the organic compound is selected from one or more organic nitrogen containing compounds.

21. The method of claim 20 wherein the one or more organic nitrogen containing compounds is selected from one or more amines.

22. The method of claim 21 wherein at least one of the amines is an aliphatic amine.

23. The method of claim 22 wherein the aliphatic amine contains one or more hydroxyl groups.

24. The method of claim 6 wherein the decomposition of the organic complex is accomplished by calcination.

25. The method of claim 7 wherein the decomposition of the organic complex is accomplished by calcination.

26. The method of claim 6 wherein the decomposition of the organic complex is accomplished by pyrolysis.

27. The method of claim 7 wherein the decomposition of the organic complex is accomplished by pyrolysis.

28. The method of claims 1, 2, 3, 4 or 5 wherein the reduced metal content ranges from about 2.5 to about 80 wt % based on the whole reduced catalyst.

29. The method of claims 1, 2, 3, 4 or 5 wherein the catalytic metal comprises one or more metals of transition Group VIII.

30. The method of claim 29 wherein the catalytic metal additionally comprises at least one additional catalytic metal selected from the group consisting of transition Group 1B, Group IIA, and mixtures thereof.

31. The method of claim 30 wherein the catalytic metal is nickel.

32. The method of claim 28 wherein the catalytic metal is nickel.

33. The method of claim 32 wherein the reduced metal content ranges from about 10 to about 65 wt % based on the whole reduced catalyst and the metal is nickel.

34. The method of claims 1, 2, 3, 4 or 5 wherein the molar ratio of primary amine to polyalkylene glycol is in the range of about 10:1 to 0.5 to 1.

35. The method of claim 34 wherein the primary amine compound is of the general formula $$R^1—NH_2$$

Wherein $R^1$ is selected from the group consisting of secondary and tertiary alkyl radicals having 3 to 8 carbon atoms, cycloalkyl radicals having 3 to 8 carbon atoms, and mixtures thereof, and the polyalkenyl glycol is of the general formula wherein $R^2$, $R^3$, $R^4$ and $R^5$ are each independently selected from the group consisting of hydrogen, C1 to C4 alkyl radicals and C3 to C8 cycloalkyl radicals with the proviso that if the carbon atom of $R^1$ directly attached to the nitrogen atom is a secondary alkyl radical, at least one of $R^2$ and $R^3$ directly bonded to the carbon which is bonded to the hydroxyl group is an alkyl or cycloalkyl radical, x and y are each positive integers independently ranging from 2 to 4, z is from 1 to 10 and the ratio of alkyl substituted primary amine to glycol is less than 2:1 when z is greater than 1.

36. The method of claims 1, 2, 3, 4 or 5 the reaction of the primary amine and the glycol is conducted at a hydrogen pressure charged at room temperature of from about zero to about 300 psig, at a temperature of about 150° C. to about 350° C., at a total reactor reaction pressure at operating temperature of about 50 to 1500 psig, for from about 0.5 to 24 hours.

37. The method of claim 36 wherein the hydrogen pressure charged at room temperature is about 20 to about 200 psig the temperature is about 160° C. to about 300° C., the total reactor pressure at operating temperature is about 50 to 1000 psig and the reaction time of from about 1 to about 12 hours.

38. The method of claim 36 wherein the hydrogen pressure charged at room temperature is about 20 to about 150 psig the temperature is about 180° C. to about 225° C., the total reactor reaction pressure at operating temperature is about 50 to 500 psig, reaction time is about 2 to about 8 hours and the primary amine to glycol ratio is about 3:1 to about 1:1.

39. The method of claim 36 wherein the primary amine is tertiary-butyl amine and the glycol is diethylene glycol.

* * * * *